(12) United States Patent
Renzi et al.

(10) Patent No.: US 7,129,267 B2
(45) Date of Patent: Oct. 31, 2006

(54) METHODS FOR SHP1 MEDIATED NEUROPROTECTION

(75) Inventors: Michael Renzi, Harleyville, PA (US); Navneeth Thirumalai, Kendall Park, NJ (US); Linda Jolliffe, Hillsborough, NJ (US); Francis X. Farrell, Doylestown, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 560 days.

(21) Appl. No.: 10/386,243

(22) Filed: Mar. 11, 2003

(65) Prior Publication Data

US 2003/0232749 A1 Dec. 18, 2003

Related U.S. Application Data

(60) Provisional application No. 60/363,440, filed on Mar. 11, 2002.

(51) Int. Cl.
A61K 31/381 (2006.01)
A61K 31/426 (2006.01)
A61K 31/427 (2006.01)

(52) U.S. Cl. ...................................... 514/438; 514/369
(58) Field of Classification Search ................ 514/438, 514/369
See application file for complete search history.

(56) References Cited

U.S. PATENT DOCUMENTS

| | | | | |
|---|---|---|---|---|
| 5,643,575 | A | 7/1997 | Martinez et al. | 424/194.1 |
| 5,688,679 | A | 11/1997 | Powell | 435/240.2 |
| 5,965,558 | A | 10/1999 | Mjalli et al. | 514/249 |
| 6,165,783 | A | 12/2000 | Weiss et al. | 435/325 |
| 6,261,279 | B1 | 7/2001 | Demopulos et al. | 604/500 |

FOREIGN PATENT DOCUMENTS

| | | |
|---|---|---|
| EP | 0 640 619 | 3/1995 |
| EP | 1 064 951 | 1/2001 |
| WO | WO 94/12650 | 6/1994 |
| WO | WO 98/05363 | 2/1998 |
| WO | WO 99/05268 | 2/1999 |
| WO | WO 99/05440 | 2/1999 |
| WO | WO 99/11781 | 3/1999 |
| WO | WO 99/38890 | 8/1999 |
| WO | WO 99/66054 | 12/1999 |
| WO | WO 01/75164 A2 | 10/2001 |

OTHER PUBLICATIONS

Brines ML et al. Erythropoietin crosses the blood-brain barrier to protect against experimental brain injury. Proc Natl Acad Sci, USA, Sep. 12, 2000, 97(19): 10526-10531.*
Renzi MJ et al. Erythropoietin down regulates SHP1 and induces a sustained activation of ERK1/ERK2 in primary cortical neurons. Blood, Nov. 16, 2001, 98(11 part 1): 77a, meeting abstract.*
Siren AL et al. Erythropoietin prevents neuronal apoptosis after cerebral ischemia and metabolic stress. Proc Natl Acad Sci, USA, Mar. 27, 2001, 98(7): 4044-4049.*
Copy of the PCT International Search Report dated Oct. 30, 2003 (PCT/US03/07200).
Barbone, F.P., et al., "New epoetin molecules and novel therapeutic approaches," Nephrol Dial Transplant, 1999, 14(Suppl. 2), 80-84.
Bittorf, T., et al., "SHP1 protein tyrosine phosphatase negatively modulates erythroid differentiation and suppression of apoptosis in J2E erythroleukemic cells," Biol. Chem., Oct. 1999, 380, 1201-1209.
Horvat, A., et al., "A novel role for protein tyrosine phosphatase SHP in controlling glial activation in thenormal and injured nervous system," J. Neurosci., 2001, 21, 865-874.
Alafaci, et al., "Effect of recombinant human erythropoietin on cerebral ischemia following experimental subarachnoid hemorrhage," Eur. J. Pharmacol., 2000, 406, 219-255.
Alessandrini, A., et al., "MEK1 protein kinase inhibition protects against damage resulting from focal cerebral ischemia," PNAS USA, 1999, 96, 12866-12869.
Bernaudin, M., et al., "A potential role for erythropoietin in focal permanent cerebral ischemia in mice," J. of Cereb. Blood Flow & Metab., 1999, 19, 643-651.
Bittorf, T., et al., "Induction of erythroid proliferation and differentiation by a trophoblast-specific cytokine involves activation of the JAK/STAT pathway," J. Mol. Endocrinol., 2000, 25, 253-262.
Brines, M.L., et al., "Erythropoietin crosses the blood-brain barrier to protect against experimental brain injury," PNAS USA, 2000, 97, 10526-10531.
Brummelkamp, T.R., et al., "A system for stable expression of short interfering RNAs in mammalian cells," Science, Apr. 19, 2002, 296, 550-553.
Cui, Y., et al., "Regulation of neutrophil responses by phosphotyrosine phosphatase," J. of Immunol., 1994, 152, 5420.
Damen, J.E., et al., "Erythropoietin stimulates the tyrosine phosphorylation of Shc and its association with Grb2 and a 145-Kd tyrosine phosphorylated protein," Blood, Oct. 15, 1993, 82(8), 2296-2303.

(Continued)

Primary Examiner—Janet L. Andres
Assistant Examiner—Kimberly A. Ballard

(57) ABSTRACT

The effect of EPO on the phosphorylation of the EPO receptor, the activation of the MAP Kinase pathway, and the expression of SHP-1 were analyzed. EPO was observed to cause a decrease in the expression of its negative regulator SHP-1. The decrease observed at both the mRNA and protein level was dose dependent and persisted as long as 24 hr following EPO treatment. EPO can down regulate the expression of its own negative regulator as a means for increased potency in neurons. Assays were generated to identify compounds that are useful in regulating SHP1 activity in neural cells.

1 Claim, 7 Drawing Sheets

OTHER PUBLICATIONS

Digicaylioglu, M., et al., "Erythropoietin-mediated neuroprotection involved cross-talk between Jak2 and NF-Kb signaling cascades," *Nature*, Aug. 9, 2001, 415, 641-647.

Digicaylioglu, M., et al., "Localization of specific erythropoietin binding sites in defined areas of the mouse brain," *Proc. Natl. Acad. Sci. USA*, Apr. 1995, 92, 3717-3720.

Elbashir, S.M., et al., "RNA interference is mediated by 21- and 22-nucleotide RNAs," *Genes & Dev.*, 2001, 15, 188-200.

Fire, A., et al., "Potent and specific genetic interference by double-stranded RNA in caenorhabditis elegans," *Nature*, Feb. 19, 1998, 391, 806-811.

Gautier, C., et al., "α-DNA IV: α-anomeric tetrathymidylates covalently linked to intercalating oxazolopyridocarbazole. Synthesis, physicochemical properties and poly (rA) binding," *Nucleic Acids Res.*, 1987, 15(16), 6625-6641.

Goeddel, Gene Expression Technology: Methods in Enzymology, *Academic Press*, San Diego, CA, 1990, 185.

Goodman, et al., *The Pharmacological Basis of Therapeutics*, 6th Ed., p. 244.

Hammond, S.M., et al., "An RNA-directed nuclease mediates post-transcriptional gene silencing in Drosophila cells," *Nature*, Mar. 16, 2000, 404, 293-296.

Hanisch, U.-K., et al., "The protein tyrosine kinase inhibitor AG126 prevents the massive microglial cytokine induction by pneumococcal cells walls," *Eur. J. Immunol.*, 2001, 31, 2104-2115.

Inoue, H., et al., "Sequence-dependent hydrolysis of RNA using modified oligonucleotide splints and RNase H," *FEBS Lett.*, 1987, 215, 327-330.

Inoue, H., et al., "Synthesis and hybridization studies on two complementary nona(2'-O-methyl)ribonucleotides," XP000570336, *Nucleic Acids Res.*, 1987, 15(15), 6131-6148.

Juul, S.E., et al., "Erythropoietin and erythropoietin receptor in the developing human central nervous system," *Pediatr. Res.*, 1998, 43(1), 40-49.

Karminski-Zamola, G., et al., "Synthesis of some furyl- and thienylacrylates or diacrylates and acrylic acids by the palladium catalysed vinylation of substituted bromofurans and bromothiophenes," *Heterocycles*, 1994, 38(4), 759-767.

Komatsu, N., et al., "Establishment and characterization of an erythropoietin-dependent subline, UT-7/EPO, derived from human leukemia cell line, UT-7," *Blood*, Jul. 15, 1993, 82(2), 456-464.

Koshimura, K., et al., "Effects of erythropoietin on neuronal activity," *J. of Neurochem.*, 1999, 72, 2565-2572.

Krautwald, S., et al., "Involvement of the protein tyrosine phosphatase SHP-1 in RAS-mediated activation of the mitogen-activated protein kinase pathway," *Mol. And Cell. Biol.*, Nov. 1996, 16(11), 5955-5963.

Lam, K.S., "Application of combinatorial library methods in cancer research and drug discovery," *Anti-Cancer Drug Des.*, 1997, 12, 145-167.

Lanzetta, P.A., et al., "An improved assay for nanomole amounts of inorganic phosphate," *Anal. Biochem.*, 1979, 100, 95-97.

Lau, L.T., et al., "Astrocytes produce and release interleukin-1, interleukin-6, tumor necrosis factor alpha and interferon-gamma following traumatic and metabolic injury," *J. of Neurotrauma*, 2001, 18(3), 351-359.

Lecoq-Lafon, C., et al., "Erythropoietin induces the tyrosine phosphorylation of GAB1 and its association with SHC, SHP2, SHIP, and phosphatidylinositol 3-kinase," *Blood*, Apr. 15, 1999, 93(8), 2578-2585.

Lue, et al., "Involvement of microglial receptor for advanced glycation endproducts (RAGE) in Alzheimer's Disease: identification of a cellular activation mechanism," *Exp. Neurol.*, 2001, 171, 29-45.

Malešević, M., et al., "Photosynthesis of heteropolycyclic diquinolones twofold photodehydrohalogeneration reaction of benzo[1,2-b:4,5-b']dithiophene- and dithieno[3,2,-b:2',3'-d]thiophenedicarboxanilides," *Heterocycles*, 1995, 41(12), 2691-2699.

Masuda, S., et al., "Functional erythropoietin receptor of the cells with neural characteristics: comparison with receptor properties of erythroid cells," *J. Biol. Chem.*, May 25, 1993, 268(15), 11208-11216.

Mauschitz, R., et al., "Self-regulation of the endothelin receptor system in choriocarcinoma cells," *Biochem. et Biophys. Acta*, 2000, 1502, 224-234.

Mizuno, K., et al., "SHP-1 is involved in neuronal differentiation of P19 embryonic carcinoma cells," *FEBS Lett.*, 1997, 417, 6-12.

Morishita, E., et al., "Erythropoietin receptor is expressed in rat hippocampal and cerebral cortical neurons, and erythropoietin prevents *in vitro* glutamate-induced neuronal death," *Neuroscience*, 1997, 76(1), 105-116.

Morishita, E., et al., "Anti-erythropoietin receptor monoclonal antibody: epitope mapping, quantification of the soluble receptor, and detection of the solubilized transmembrane receptor and the receptor-expressing cells," *Blood*, Jul. 15, 1996, 88(2), 465-471.

Moss, E.G., "RNA interference: It's a small RNA world," *Curr. Biol.*, 2001, 11, R772-R775.

Murray, B., et al., "Inhibition of the P44/42 MAP kinase pathway protects hippocampal neurons in a cell-culture model of seizure activity," *PNAS USA*, Sep. 1998, 95, 11975-11980.

Nagai, A., et al., "Erythropoietin and erythropoietin receptors in human CNS neurons, astrocytes, microglia, and oligodendrocytes grown in culture," *J. of Neuropathol. Exp. Neurol.*, Apr. 2001, 60(4), 386-392.

Namura, S., et al., "Intravenous administration of MEK inhibitor U0126 affords brain protection against forebrain ischemia and focal cerebral ischemia," *PNAS USA*, Sep. 25, 2001, 98(20), 11569-11574.

Oritz, A., et al., "Nerve growth factor treatment of cortical focal ischemia," *Soc. Neurosci. Abs.*, 1990, 386.18, p. 942.

Otto, D., et al., "Basic fibroblast growth factor and nerve growth factor administered in gel foam rescue medial septal neurons after fimbria fornix transaction," *J. of Neurosci. Res.*, 1989, 22, 83-91.

Plutzky, J., et al., "Isolation of a src homology 2-containing tyrosine phosphatase," *Proc. Natl. Acad. Sci. USA*, 1992, 89(3), 1123-1127 GenBank M77273 & GenBank Protein ID No. AAA36610, PUBMED 1736296, 3 pages.

Plutzky, J., et al., "Isolation of a src homology 2-containing tyrosine phosphatase," *Proc. Natl. Acad. Sci. USA*, Feb. 1992, 89, 1123-1127.

Ribatti, D., et al., "Human erythropoietin induces a pro-angiogenic phenotype in cultured endothelial cells and stimulates neovascularization in vivo," *Blood*, Apr. 15, 1999, 93(8), 2627-2636.

Šafarik, J.B., et al., "Convenient synthesis $^1$H, $^{13}$C NMR study and x-ray crystal structure determination of some new disubstituted thiophenes," *Spectroscopy Letters*, 1999, 32(3), 443-462.

Sakanaka, M., et al., "In vivo evidence that erythropoietin protects neurons from ischemic damage," *PNAS USA*, Apr. 1998, 95, 4635-4640.

Sinor, A.D., et al., "Erythropoietin protects cultured cortical neurons, but not astroglia, from hypoxia and AMPA toxicity," *Neurosci. Lett.*, 2000, 290, 213-215.

Stanciu, M., et al., "Persistent activation of ERK contributes to glutamate-induced oxidative toxicity in a neuronal cell line and primary cortical neuron cultures," *J. Biol. Chem.*, Apr. 21, 2000, 275(16), 12200-12206.

Struder, L., et al., "Enhanced proliferation, survival, and dopaminergic differentiation of CNS precursors in lowered oxygen," *J. Neurosci.*, Oct. 1, 2000, 20(19), 7377-7383.

Takeuchi, A., et al, "Mactophage colony-stimulating factor is expressed in neuron and microglia after focal brain injury," *J. of Neurosci. Res.*, 2001, 65, 38-44.

Takeuchi,A., et al., "Microglial NO induces delayed neuronal death following acute injury in the striatum," *Eur. J. of Neurosci.*, 1998, 10, 1613-1620.

Weintraub, H., et al., "Anti-sense RNA as a molecular tool for genetic analysis," *Reviews—Trends in Genetics*, Jan. 1985, 22-25.

Westenfelder, C., et al., "Human, rat, and mouse kidney cells express functional erythropoietin receptors," *Kidney Int.*, 1999, 55, 808-820.

Williams, L.R.., et al., "Continuous infusion of nerve growth factor prevents basal forebrain neuronal death after fimbria fornix transaction," *Proc. Natl. Acad. Sci. USA*, Dec. 1986, 83, 9231-9235.

Zamore, P.D., et al., "RNAi: Double-stranded RNA directs the ATP-dependent cleavage of mRNA at 21 to 23 nucleotide intervals," *Cell*, Mar. 31, 2000, 101, 25-33.

Brumell et al. "Regulation of Src Homology 2-containing Tyrosine Phosphatase 1 during Activation of Human Neutrophils", *J. Biol. Chem.*, Jan. 10, 1997, vol. 272, No. 2, pp. 875-882.

* cited by examiner

METHODS FOR SHP1 MEDIATED NEUROPROTECTION

This patent application claims priority from U.S. Provisional patent application No. 60/363,440 filed Mar. 11, 2002 and entitled "Methods and Compositions for SHP1 mediated Neuroprotection."

BACKGROUND OF THE INVENTION

The present invention provides methods to use SHP1 modulators for neuroprotection and assays capable of identifying SHP1 modulators.

FIELD OF THE INVENTION

Erythropoietin (EPO) is responsible for the maintenance, increase and terminal differentiation of erythroid progenitor cells. Erythropoiesis is controlled by the production of erythropoietin in the kidney as a function of oxygen tension in the blood. Recent data has shown that other cell types, including endothelial cells [26], kidney cells [33] and neuronal cells [22], also contain functional EPO receptor (EPOR).

Several lines of evidence support the function of EPO as a neuroprotective molecule. First, both EPO and its receptor have been found in neural tissues [11], including rat hippocampal neurons and subsets of neurons in the rat cerebral cortex [21]. Second, in a series of in vitro experiments, EPO has been shown to prevent the death of neurons in response to a variety of insults including glutamate toxicity and hypoxia [21, 28]. In addition, the neuroprotective effects of EPO have been demonstrated in several in vivo models of CNS injury. Intraventricular administration of EPO significantly decreased the damage observed in an ischemic gerbil model [27], and in a mouse model of middle cerebral artery occlusion [3]. Recently, reports have shown that EPO administered systemically can cross the blood brain barrier and have a protective effect in in vivo models of stroke, blunt trauma [5] and sub-arachnoid hemorrhage-induced acute cerebral ischemia [1]. In addition, EPO has been suggested to be the factor responsible for the increased survival, differentiation and proliferation of neuronal stem cells that are cultured under conditions of low oxygen [30]. These results suggest that EPO can be useful as a neuroprotective molecule for the treatment of nervous system conditions, such as stroke, and other neurodegenerative diseases.

U.S. Pat. No. 6,165,783 states that "[t]he erythropoietin may be exogenously applied to the multipotent neural stem cells, or alternatively, the cells can be subjected to hypoxic insult which induces the cells to express erythropoietin."

EPO exerts its biological effect by binding to preexisting receptor dimers located on the cell surface and inducing a conformational change in the EPO receptor, EPOR. The change in EPOR conformation results in the activation of JAK2 and the subsequent phosphorylation of tyrosine residues on the EPO receptor and other intracellular proteins such as ERKs, Shc and Stat5 [6, 4]. The change in EPOR conformation also results in recruitments of SH2 domain containing proteins to the receptor complex, including the SH2 containing protein tyrosine phosphatase (PTPase) SHP1, also known as SH-PTP1, PTP1C, HCP or SHP, which dephosphorylates JAK2 and subsequently inactivates JAK2. Due to the presence of high levels of SHP1 in all hematopoietic cell lineages at all stages of hematopoietic cell differentiation, phosphorylation of EPO is transient with the loss of detectable phosphorylation on tyrosine residue(s) of EPOR within thirty minutes after the initial binding of EPO to EPOR. While the function of EPO to protect neurons from cell death is consistent with the function of EPO in hematopoietic cells, the potency of the effect of EPO on neuronal cells increased significantly as compared with hematopoietic cells. EPO has been observed to be effective at pM concentrations in neurons while nM levels of EPO are required to elicit the same effects in hematopoietic cells [27, 13].

The mechanism for increased potency of EPO in neuronal cells is not clear. Previous reports have indicated, that the EPOR expressed in neurons is identical in sequence to that found in hematopoietic cells, including all potential sites of tyrosine phosphorylation, and that EPOR expressed in neurons has a lower affinity for EPO [18]. While the possibility exists that the EPOR is different in neurons due to variations in post-translational modifications, the relative low affinity of EPO for the EPOR in neurons and the observation that EPO activates similar signaling pathways to neuronal cells similar to those in hematopoietic cells make it unlikely that changes in EPOR alone accounts for the increased potency of EPO in neuronal cells.

Little is known about the role of SHP1 in EPOR activated signal transduction pathway in cells of the nervous system in part because there is little information concerning the expression or function of SHP1 in CNS. SHP1 has been reported to be present in specific neuron subtypes [10] and to negatively regulate specific functions in neural cell lines [20]. Stimulation of neutrophils with chemotactic peptides is known to result in the activation of tyrosine kinases that mediate neutrophil responses (Cui et al., J. Immunol., 1994) and the PTPase activity of SHP1 modulates agonist-induced activity by reversing the effects of tyrosine kinases activated in the initial phases of cell stimulation. U.S. Pat. No. 6,261,279 suggests that "agents that could stimulate PTPase activity could have potential therapeutic applications as anti-inflammatory mediators." Although it has been reported that SHP1 can act as a positive signal in RAS-mediated activation of the mitogen-activated protein kinase pathway, it is not known what regulatory role SHP1 plays in EPOR activated signal transduction pathway in cells of the nervous system.

Understanding the role of SHP1 in EPOR activated signal transduction pathway in cells of the nervous system can shed light on the mechanism of the neuroprotection function of EPO, which in turn can help the design and identification of novel neuroprotective molecules.

SUMMARY OF THE INVENTION

It has now been discovered that treating cells of the nervous system with EPO results in decreased expression of SHP1 in the cell. This down regulation of SHP1 then prevents the timely dephosphorylation of the EPOR thus allowing for a sustained activation of both the EPOR itself and downstream targets such as ERK1/ERK2. The sustained activation of EPOR can explain the high potency of EPO in the cells of nervous system.

In one general aspect, the invention therefore provides a method for treating a nervous system condition related to EPOR in a subject in need thereof, comprising the step of administering to the subject a therapeutically effective dose of a composition that decreases the tyrosine phosphatase activity of a SHP1 in a cell of the nerve system of the subject. For example, the subject can be in need of treatment for neuroprotection.

In other general aspects, the invention provides a method for treating a nervous system condition related to EPOR in a subject in need thereof, comprising the step of administering to the subject a therapeutically effective dose of a composition that decreases the expression of a SHP1 in a cell of the nerve system of the subject. For example, the composition comprises an antisense nucleic acid or a siRNA molecule specific for an SHP1 gene and the antisense nucleic acid or siRNA molecule specifically suppresses SHP1 gene expression.

An additional general aspect of the invention is a method of identifying a compound useful for treating a nervous system condition related to EPOR, comprising the steps of:
1) contacting a test compound with an SHP1 protein or an active fragment thereof; and
2) determining the ability of the test compound to decrease the tyrosine phosphatase activity of SHP1.

Further general aspect of the invention is a method of identifying a compound useful for treating a nervous system condition related to EPOR, comprising the steps of:
 a) contacting a test compound with a regulatory sequence for a SHP1 gene or a cellular component that binds to the regulatory sequence for a SHP1 gene; and
 b) determining whether the test compound decreases the expression of a gene controlled by said regulatory sequence.

Yet another general aspect of the invention is a method of identifying a compound useful for treating a nervous system condition related to EPOR, comprising the steps of:
 a) combining a test compound, a labeled ligand for a SHP1 protein, and a SHP1 protein or an active fragment thereof; and
 b) measuring the binding of the test compound to the SHP1 protein or active fragment thereof by a reduction in the amount of labeled ligand binding to the SHP1 protein or active fragment thereof.

In preferred embodiments of the invention, the methods of identifying a compound useful for treating a nervous system condition related to EPOR, further comprise the steps of
 a) contacting a neuronal cell with the test compound;
 b) inducing neurotoxicity in the neuronal cell;
 c) assaying the cell survival rate in the presence of the test compound, and comparing the cell survival rate with that of a control wherein the neuronal cell is not treated with the test compound.

Other aspects, features and advantages of the invention will be apparent from the following disclosure, including the detailed description of the invention and its preferred embodiments and the appended claims.

Figure 1:
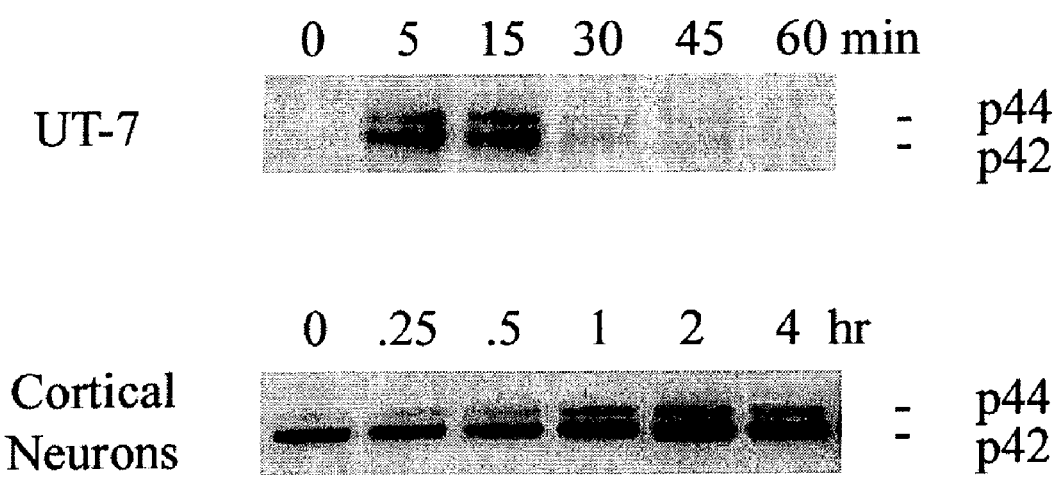
FIG. 1: Illustrates a sustained phosphorylation of ERKs in neurons treated with EPO as compared to that in hematopoietic cells treated with EPO. Primary cortical neurons and hematopoietic cells UT-7 were treated with EPO for the indicated time then harvested. Cell extracts were analyzed by SDS-PAGE Western blots, probed with antibodies against ERK1/ERK2 (p44/42) MAPK. The time course of ERK1/ERK2 phosphorylation in neurons or UT-7 cells treated with EPO is plotted.

An illustration of increased potency of EPO in neurons due to EPO mediated down regulation of SHP1. In hematopoietic cells (5a), EPOR activation is initiated by EPO binding to the receptor and the subsequent activation of JAK2 and phosphorylation of specific tyrosine residues located on the EPOR. Inactivation (termination) of EPOR signaling is achieved, at least in a large part, by the removal of these phosphate groups by the tyrosine phosphatase SHP1. Thus, the balance between these two opposing mechanisms determines the amount of activated EPOR in response to a specific concentration of EPO. In cells of the nervous system (5b), binding of EPO to EPOR causes a rapid down-regulation of the expression of SHP1. The decrease in SHP-1 protein levels present in the cytosol results in less dephosphorylation of EPOR, and shifts the activation/inactivation balance toward activation. Therefore at a given concentration of EPO, EPORs are more likely to be activated than inactivated leading to an increased potency for EPO in these cells

DETAILED DESCRIPTION OF THE INVENTION

All publications cited below are hereby incorporated by reference. Unless defined otherwise, all technical and scientific terms used herein have the same meaning as commonly understood to one of ordinary skill in the art to which this invention pertains.

The following are abbreviations that are at times used in this specification below:

bp = base pair
cDNA = complementary DNA
CNS = central nervous system
EPO = erythropoietin
EPOR = erythropoietin receptor
MAP kinase = mitogen-activated protein kinase
PAGE = polyacrylamide gel electrophoresis
PCR = polymerase chain reaction
PTPase = protein tyrosine phosphatase
SDS = sodium dodecyl sulfate
SH2 = src homology 2
SiRNA = small interfering RNA
UTR = untranslated region The terms "including," "comprising", "containing" and "having" are used herein in their open, non-limiting sense.

An "activity", a "biological activity", or a "functional activity" of a polypeptide or nucleic acid of the invention refers to an activity exerted by a polypeptide or nucleic acid molecule of the invention as determined in vivo or in vitro, according to standard techniques. Such activities can be a direct activity, such as an association with or an enzymatic activity on a second protein, or an indirect activity, such as a cellular signaling activity mediated by interaction of the protein with a second protein.

An exemplary biological activity associated with EPOR is its ability to bind EPO. Another exemplary biological activity of EPOR is the ability of EPOR, upon binding of EPO, to transduce a signal to the target proteins such as JAK2, ERKs, Shc and Stat5. Yet, another exemplary biological activity of EPOR is the ability of EPOR, upon binding of EPO, to recruit SH2 domain containing proteins, including SHP 1, to the receptor complex.

An exemplary activity of SHP1 is the tyrosine phosphatase activity of SHP1, for example, the ability of SHP1 to dephosphorylate the phosphorylated JAK2. Another exemplary activity of SHP1 is the ability of SHP1 to bind to a tyrosine residue in the cytoplasmic domain of EPOR upon the binding of EPO to EPOR.

A "nervous system condition related to EPOR" shall include a disorder or disease associated with insufficient activity of EPOR in the nervous system, and conditions that accompany this disorder or disease. "Insufficient activity of EPOR" refers to either 1) the absence of EPOR expression in cells which normally express EPOR; 2) decreased EPOR expression; 3) decreased activity of EPOR per unit of the EPOR protein; or 4) mutations leading to constitutive inactivation of one or more EPOR biological activities. Exemplary nervous system conditions related to EPOR, include, but are not limited to conditions that are the result of a seizure disorder, multiple sclerosis, stroke, hypotension, cardiac arrest, ischemia, myocardial infarction, inflammation, aging or cognitive dysfunction, radiation damage, cerebral palsy, neurodegenerative disease, Alzheimer's disease, Parkinson's disease, Leigh disease, AIDS dementia, memory loss, amyotrophic lateral sclerosis, alcoholism, mood disorder, anxiety disorder, attention deficit disorder, autism, Creutzfeld-Jakob disease, brain or -spinal cord trauma, heart-lung bypass, glaucoma, retinal ischemia, or retinal trauma.

"Gene therapy" means the introduction of a functional gene, genes, or a nucleic acid fragment from some source by any suitable means into a living cell to correct for a genetic defect.

The term "regulatory region" or "regulatory sequence" is intended to include promoters, enhancers and other expression control elements (e.g., polyadenylation signals, and ribosome binding site (for bacterial expression) and, an operator). Such regulatory sequences are described and can be readily determined using a variety of methods known to those skilled in the art (see for example, in Goeddel, *Gene Expression Technology: Methods in Enzymology* 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences).

"Cells of the nervous system" refers to cells that are specifically related to the nervous system of an animal. For example, a "cell of the nervous system" can be a "neuron" or a "nerve cell", which is an excitable cell specialized for the transmission of electrical signals over long distances. Neurons receive input from sensory cells or other neurons and send output to muscles or other neurons. Exemplary "neurons" include a "sensory neuron" that has sensory input, a "motoneuron" that has muscle outputs, or "interneuron" that connects only with other neurons. A "cell of the nervous system" can also be a specialized non-neuronal nervous cell, for example a glial cell, which is a cell that surrounds a neuron, providing mechanical and physical support and electrical insulation between neurons. Examples of glial cells include, but are not limited to, microglial cells and astrocytes.

The term "subject" as used herein, refers to an animal, preferably a mammal, most preferably a human, who is the object of treatment, observation or experiment.

As used herein, the term "substantially purified" means that the protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals that are involved in the synthesis of the protein. Accordingly such preparations of the protein have less than about 30%, 20%, 10%, 5% (by dry weight) of chemical precursors or compounds other than the polypeptide of interest.

As used herein, "treating" a disorder means eliminating or otherwise ameliorating the cause and/or effects thereof. To "inhibit" or "inhibiting" the onset of a disorder means preventing, delaying or reducing the likelihood of such onset.

The term "composition" is intended to encompass a product comprising the specified ingredients in the specified amounts, as well as any product which results, directly or indirectly, from combinations of the specified ingredients in the specified amounts.

As used herein, "erythropoietin" or "EPO" shall include those polypeptides and proteins that have the biological activity of recombinant human erythropoietin (rhEPO), as well as erythropoietin analogs, erythropoietin isoforms, erythropoietin mimetics, erythropoietin fragments, hybrid erythropoietin proteins, fusion proteins oligomers and multimers of the above, homologues of the above, glycosylation pattern variants of the above, and muteins of the above, regardless of the biological activity of same, and further regardless of the method of synthesis or manufacture thereof including, but not limited to, recombinant (whether produced from cDNA or genomic DNA), synthetic, transgenic, and gene activated methods. Specific examples of erythropoietin include, Epoetin alfa (EPREX®, ERYPO®, PROCRIT®), novel erythropoiesis stimulating protein (NESP™, ARANESP™, darbepoetin alfa) such as the hyperglycosylated analog of recombinant human erythropoietin (Epoetin) described in European patent application EP 640619, human erythropoietin analog (such as the human serum albumin fusion proteins described in the international patent application WO 99/66054), erythropoietin mutants described in the international patent application WO 99/38890, erythropoietin omega, which may be produced from an Apa I restriction fragment of the human erythropoietin gene described in U.S. Pat. No. 5,688,679, altered glycosylated human erythropoietin described in the international patent application WO 99/11781 and EP 1064951, PEG conjugated erythropoietin analogs described in WO 98/05363 or U.S. Pat. No. 5,643,575. Specific examples of cell lines modified for expression of endogenous human erythropoietin are described in international patent applications WO 99/05268 and WO 94/12650. The generally preferred form of EPO is purified recombinant human EPO (rhEPO), currently formulated and distributed under the trademarks of EPREX®, ERYPO®, PROCRIT® or ARANESP™.

The term "SHP 1", "SH-PTP1", "PTP1 C", "HCP" or "SHP" all refers to a src homology 2-containing tyrosine phosphatase that is capable of removing a phosphate group from a phosphorylated protein at a tyrosine residue, and comprises an amino acid sequence that has greater than about 60% amino acid sequence identity, to human SHP1 (Plutzky et al., 1992. *Proc. Natl. Acad. Sci. U.S.A.* 89 (3), 1123–1127, GenBank Protein_Id No.: AAA36610); is capable of binding to antibodies, e.g., polyclonal or monoclonal antibodies, raised against a human SHP1 protein described herein; or is encoded by a polynucleotide that specifically hybridizes under high stringent hybridization conditions to a nucleic acid molecule having a sequence that has greater than about 80% nucleotide sequence identity to human SHP1 cDNA (GenBank nucleotide Accession No: M77273).

Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C.

In preferred embodiments, the SHP1 is a polypeptide having greater than 80, 85, 90, or 95 percent amino acid sequence identity to human SHP 1. In other preferred embodiments, the SHP1 is a polypeptide encoded by a polynucleotide that specifically hybridizes under stringent hybridization conditions to a nucleic acid molecule having a sequence that has greater than 80, 85, 90, or 95 percent nucleotide sequence identity to human SHP1 cDNA. Exemplary SHP1 include SHP1 orthologs that have been identified in human, rat, mouse, and other animals, including pig and monkey.

An "active fragment of SHP1" refers to a fragment of SHP1 that comprises an amino acid sequence that has greater than about 90% amino acid sequence identity, preferably about 95% amino acid sequence identity, to the sequence of at least ten consecutive amino acids of a SHP1, and such an active fragment of SHP1 is still capable of removing a phosphate group from a phosphorylated protein at a tyrosine residue.

"Promoter" means a regulatory sequence of DNA that is involved in the binding of RNA polymerase to initiate transcription of a gene. A "gene" is a segment of DNA involved in producing a peptide, polypeptide, or protein, including the coding region, non-coding regions preceding ("5'UTR") and following ("3'UTR") coding region, as well as intervening non-coding sequences ("introns") between individual coding segments ("exons"). A promoter is herein considered as a part of the corresponding gene. Coding refers to the representation of amino acids, start and stop signals in a three base "triplet" code. Promoters are often upstream ("5'to") of the transcription initiation site of the gene.

Methods of Treatment

In hematopoietic and nonhematopoietic cells, including neurons, SHP-1 decreases the level of EPOR phosphorylation by binding to a tyrosine residue in the cytoplasmic domain of the EPOR and dephosphorylating JAK2, which is phosphorylated upon EPO binding to the EPOR [7]. In hematopoietic cells, the phosphorylation of EPOR is transient largely due to the presence of high levels of SHP1 activity inside the cell. The present invention shows that although EPO utilizes similar signaling pathways in neurons and hematopoietic cells, the temporal signaling events are different. EPO down-regulates SHP1 expression in cells of nervous system resulting in a sustained phosphorylation of the EPO receptor following EPO binding. Moreover, a sustained phosphorylation of the downstream signaling proteins ERK1/ERK2 is observed following EPO binding and EPO receptor activation. These observations provide insight as to why EPO has increased potency in neurons.

In one general aspect, the invention provides a method for treating a nervous system condition related to EPOR in a subject in need thereof, comprising the step of administering to the subject a therapeutically effective dose of a composition that decreases the tyrosine phosphatase activity of a SHP1 in a cell of the nervous system of a subject. In a preferred embodiment, the subject receiving treatment is in need of neuroprotection. The neuroprotective effects of EPO are useful in individuals suffering from seizure disorders, multiple sclerosis, stroke, hypotension, cardiac arrest, ischemia, myocardial infarction, inflammation, aging or cognitive dysfunction, radiation damage, cerebral palsy, neurodegenerative disease, Alzheimer's disease, Parkinson's disease, Leigh disease, AIDS dementia, memory loss, amyotrophic lateral sclerosis, alcoholism, mood disorder, anxiety disorder, attention deficit disorder, autism, Creutzfeld-Jakob disease, brain or -spinal cord trauma, heart-lung bypass, glaucoma, retinal ischemia, or retinal trauma. In one preferred embodiment, the condition is an acute nervous system disease selected from the group consisting of ischemic stroke, hemorrhagic stroke, spinal cord injury traumatic brain injury, and the like. In another preferred embodiment, the condition is a chronic nervous system disease selected from the group consisting of Alzheimer's disease, Parkinson's disease, peripheral neuropathies, and cognitive impairment associated with coronary artery bypass graft surgery (CABG) and carotid endarterectomy (CEA).

In one preferred embodiment, the cell of the nervous system is a neuronal cell, such as a sensory neuron, a motoneuron, or interneuron. Particularly, the neuron is a primary cortical neuron, or a hippocamapal neuron. In another preferred embodiment, the cell of the nervous system is a non-neuronal cell, such as a glial cell. Particularly, the non-neuronal cells of the nervous system are microglial cells or astrocytes.

The composition that decreases the tyrosine phosphatase activity of a SHP1 in a cell of the nervous system of the subject comprises a compound that is identified by any of the compound identification methods described infra. For example, the composition can comprise a compound with the structure of formula (I), formula (II), or formula (III) or other compositions identified using the assays of the present invention and described infra.

The composition can be administered in combination with one or more neuroprotective agents. In one embodiment of this aspect, more than one compound that decreases the tyrosine phosphatase activity of a SHP1 in a cell of the nerve system of the subject can be administered to the subject. In a preferred embodiment, EPO can be administered to the subject together with a compound that that decreases the tyrosine phosphatase activity of a SHP1 in a cell of the nervous system of the subject. In yet another preferred embodiment, other known neuroprotective agents can be administered together with a compound that decreases the tyrosine phosphatase activity of a SHP1 in a cell of the nervous system of a subject.

In other general aspects, the invention provides a method for treating a nervous system condition related to EPOR in a subject in need thereof, comprising the step of administering to the subject a therapeutically effective dose of a composition that decreases the expression of a SHP1 in a cell of the nervous system of a subject. Examples of such compositions include for example, compounds that repress SHP1 transcription or translation, which can be identified by methods described infra. In addition, antisense nucleic acids or small interfering RNAs (siRNAs) can also be used to reduce the expression of SHP1 through gene therapy.

The invention is amenable to antisense nucleic acids or siRNA based strategies by reducing expression of SHP1 in cells of the nervous system of a subject. The principle of antisense nucleic acids strategies is based on the hypothesis that sequence-specific suppression of gene expression can be achieved by intracellular hybridization between mRNA and a complementary antisense species. The formation of a hybrid RNA duplex may then interfere with the processing/transport/translation and/or stability of the target SHP1 mRNA. Hybridization is required for the antisense effect to occur. Antisense strategies may use a variety of approaches including the use of antisense oligonucleotides, injection of antisense RNA and transfection of antisense RNA expression vectors. Phenotypic effects induced by antisense effects are based on changes in criteria such as protein levels, protein activity measurement, and target mRNA levels.

An antisense nucleic acid can be complementary to an entire coding strand of a SHP1 gene, or to only a portion thereof. An antisense nucleic acid molecule can also be complementary to all or part of a non-coding region of the coding strand of a SHP1 gene. The non-coding regions ("5' and 3' untranslated regions") are the 5' and 3' sequences that flank the coding region and are not translated into amino acids. Preferably, the non-coding region is a regulatory region for the transcription or translation of the SHP1 gene.

An antisense oligonucleotide of the invention can be, for example, a length of about 15, 20, 25, 30, 35, 40, 45 or 50 nucleotides or more that is complementary to the nucleotide sequence of human SHP1. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides that can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxytnethylaminomethyl-2-thiouridine, 5-carboxymethylaminomethyluracil, dihydrouracil, beta-D-galactosylqueosine, inosine, N6-isopentenyladenine, I-methylguanine, 1-methylinosine, 2,2-dimethylguanine, 2-methyladenine, 2-methylguanine, 3-methyleytosine,. 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. An antisense nucleic acid molecule can be a CC-anomeric nucleic acid molecule. A CC-anomeric nucleic acid molecule forms specific double-stranded hybrids with complementary RNA in which, the strands run parallel to each other (Gaultier et al. (1987) *Nucleic Acids Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215: 327–330).

Alternatively, the antisense nucleic acid can also be produced biologically using an expression vector into which a nucleic acid has been subcloned in an antisense orientation (i.e., RNA transcribed from the inserted nucleic acid will be of an antisense orientation to a target nucleic acid of interest). That is, a DNA molecule is operably linked to a regulatory sequence in a manner that allows for expression (by transcription of the DNA molecule) of an RNA molecule that is antisense to the mRNA encoding a SHP1 protein. Regulatory sequences operably linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. ((1986), *Reviews—Trends in Genetics, Vol.* 1(1)).

The antisense nucleic acid molecules of the invention are typically administered to a subject or generated in situ such that they hybridize with or bind to cellular mRNA and/or genomic DNA encoding a SHP1 protein to thereby inhibit expression of the protein, e.g., by inhibiting transcription and/or translation. The hybridization can be by conventional nucleotide complementarity to form a stable duplex, or, for example, in the case of an antisense nucleic acid molecule that binds to DNA duplexes, through specific interactions in the major groove of the double helix. Antisense nucleic acid molecules can be administered to the subject via direct injection or surgical implantation in the proximity of the damaged tissues or cells in order to circumvent their exclusion from the central nervous system (CNS) by an intact blood-brain barrier. Successful delivery of nucleic acid molecules to the CNS by direct injection or implantation has been documented (See e.g., Otto et al., (1989), *J. Neurosci. Res.* 22: 83–91; Goodman & Gilman's *The Pharmacological Basis of Therapeutics,* 6th ed, pp 244; Williams et al., (1986), *Proc. Natl. Acad. Sci. USA* 83: 9231–9235; and Oritz et al., (1990), *Soc. Neurosci. Abs.* 386: 18).

Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens.

The antisense nucleic acid molecules can also be generated in situ by expression from vectors described herein harboring the antisense sequence. To achieve sufficient intracellular concentrations of the antisense molecules, vector constructs in which the antisense nucleic acid molecule is placed under the control of a strong pol II or pol III promoter are preferred. In a preferred embodiment, the method of treating a pain in a subject in need thereof involves the use of small interfering RNA (siRNA). In several organisms, introduction of double-stranded RNA has proven to be a powerful tool to suppress gene expression through a process known as RNA interference. Many organisms possess mechanisms to silence any gene when double-stranded RNA (dsRNA) corresponding to the gene is present in the cell. The technique of using dsRNA to reduce the activity of a specific gene was first developed using the worm *C. elegans* and has been termed RNA interference, or RNAi (Fire, et al., (1998), *Nature* 391: 806–811). RNAi has since been found to be useful in many organisms, and recently has been extended to mammalian cells in culture (see review by Moss, (2001), *Curr Biol* 11: R772–5).

An important advance was made when RNAi was shown to involve the generation of small RNAs of 21–25 nucleotides (Hammond et al., (2000) *Nature* 404: 293–6; Zamore et al., (2000) *Cell* 101: 25–33). These small interfering RNAs, or siRNAs, may initially be derived from a larger dsRNA that begins the process, and are complementary to the target RNA that is eventually degraded. The siRNAs are themselves double-stranded with short overhangs at each end; they act as guide RNAs, directing a single cleavage of the target in the region of complementarity (Elbashir et al., (2001) *Genes Dev* 15: 188–200; Zamore et al., (2000) *Cell* 101: 25–33).

Methods of producing siRNA, 21–23 nucleotides (nt) in length from an in vitro system and use of the siRNA to interfere with mRNA of a gene in a cell or organism were described in WO0175164 A2, the contents of which is entirely incorporated herein by reference.

The siRNA can also be made in vivo from a mammalian cell using a stable expression system. For example, a vector system, named pSUPER, that directs the synthesis of small interfering RNAs (siRNAs) in mammalian cells, was recently reported (Brummelkamp et al., (2002) *Science* 296: 550–3.), and the contents of which is incorporated herein by reference.

On the pSUPER, the H1-RNA promoter was cloned in front of the gene specific targeting sequence (19-nt sequences from the target transcript separated by a short spacer from the reverse complement of the same sequence) and five thymidines (T5) as a termination signal. The resulting transcript is predicted to fold back on itself to form a 19-base pair stem-loop structure, resembling that of *C. elegans* Let-7. The size of the loop (the short spacer) is preferably 9 bp. A small RNA transcript lacking a polyadenosine tail, with a well-defined start of transcription and a termination signal consisting of five thymidines in a row (T5) was produced. Most importantly, the cleavage of the transcript at the termination site is after the second uridine yielding a transcript resembling the ends of synthetic siRNAs, that also contain two 3' overhanging T or U nucleotides. The siRNA expressed from pSUPER is able to knock down gene expression as efficiently as the synthetic siRNA.

The present invention provides a method of treating a nervous system condition related to EPOR in a subject in need thereof, comprising the steps of (a) introducing the antisense nucleic acid or siRNA that targets the mRNA of the SHP1 gene for degradation into the cell or organism; (b) maintaining the cell or organism produced (a) under conditions under which the antisense nucleic acid or siRNA interference of the mRNA of the SHP1 gene in the cell or organism occurs. The siRNA can be produced chemically via nucleotide synthesis, from an in vitro system similar to that described in WO0175164, or from an in vivo stable expression vector similar to pSUPER described herein. The siRNA can be administered similarly as that of the anti-sense nucleic acids described herein.

The present invention also provides a kit with one or more containers comprising an inhibitor for SHP1 protein tyrosine phosphatase, and a pharmaceutically acceptable diluent.

Methods are known in the art for determining therapeutically and prophylactically effective or active doses for the instant pharmaceutical composition. The term "therapeutically effective amount" or "therapeutically active amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. The term "prophylactically effective amount" or "prophylactically active amount" refers to that amount of active compound or pharmaceutical agent that inhibits in a subject the onset of a disorder as being sought by a researcher, veterinarian, medical doctor or other clinician, the delaying of which disorder is mediated by the activity of protein tyrosine phosphatases, including but not limited to, SHP 1.

Where protein delivery is contemplated, the amount of protein used in the formulations of the present invention will vary with the biological potency of the protein as well as the desired potency of the formulation, but will generally contain about 1 µg/ml to about 2000 µg/ml protein per formulation. Specifically the erythropoietin-containing formulations of the present invention may contain a "pharmaceutically active amount of erythropoietin", generally about 1000 IU/ml to about 180,000 IU/ml of erythropoietin, wherein 120,000 IU is approximately 1000 μg. The erythropoietin may be provided as an aqueous solution of a bulk reagent that is diluted into the formulation of the present invention or may be provided as a dried reagent and reconstituted using the appropriate amount of the aqueous formulation. Dried reagents include, for example, lyophilized or spray-dried erythropoietin. Where erythropoietin is provided as a bulk reagent in formulations of high potency (e.g. greater than 100,000 IU/ml), it is preferable that the erythropoietin bulk reagent be provided in a phosphate buffered solution. This is due to increased patient discomfort caused by high concentrations of citric acid buffers typically used in the preparation of recombinant human erythropoietin. Buffer exchange is achieved using methods well known in the art, such as diafiltration or dialysis to provide an EPO bulk that contains less than 1 millimolar citrate.

The amount of buffering agent useful in the pharmaceutical compositions of the present invention depends largely on the particular buffer used and the desired pH of the formulation. The concentration of buffering ions will generally range from about 10 mM to about 30 mM. Suitable buffer systems to maintain the pH range of about four to about nine include, but are not limited to, sodium citrate/citric acid, sodium acetate/acetic acid, sodium or potassium phosphate dibasic/monobasic, and any other pharmaceutically acceptable pH buffering agent(s) known in the art. The use of a buffer system of sodium phosphate dibasic and sodium phosphate monobasic is preferred. A pH-adjusting agent such as, but not limited to, hydrochloric acid, citric acid, sodium hydroxide, or a salt of any of these, in particular sodium citrate, may be added to the formulations to adjust the formulation pH to within the desired formulation pH range. One goal for these formulations is to minimize the patient discomfort associated with subcutaneous administration of the citrate-buffered formulations. Therefore phosphate buffer systems are particularly preferred in all formulations of the present invention, both in the aqueous protein bulk reagent and in the formulation buffer component.

One or more ionic tonicity agents may be used in the formulations of the present invention. An ionic tonicity agent is any agent capable of rendering the formulations of the present invention iso-osmotic or nearly iso-osmotic with human blood and carries a positive or negative charge in aqueous solutions. Typical suitable tonicity agents are well known in the art, and include but are not limited to sodium chloride, potassium chloride, ammonium sulfate, glycine, or other amino acids. The preferred tonicity agents of the present invention include, but are not limited to, NaCl, KCl, and glycine, said agent being used at a concentration in the range of about 0 to about 170 millimolar. Use of sodium chloride as a tonicity agent is preferred in the formulations of the present invention at a concentration of about 75 mM to about 100 mM. The type of tonicity agent and its concentration may influence the properties of the formulation. In formulations containing more than one tonicity agent, the total concentration of tonicity agents is generally less than 200 mM.

The formulations of the present invention may be prepared by admixing the formulation reagents in an aqueous solution such that the components are mixed substantially uniformly so that none of the components are localized. Advantageously all of the formulation components, except the protein component, can be prepared and adjusted to conditions suitable for the protein prior to the addition of the protein component. Alternatively, the protein bulk reagent may be diafiltered into an appropriate buffer system, preferably phosphate buffer, and the other reagents may be added to the protein bulk, and the bulk protein concentration can be adjusted appropriately to the desired potency.

The formulations of the present invention are administered to a subject in need thereof via parental administration including intravenous administration. Particular routes of parenteral administration include, but are not limited to, intramuscular, subcutaneous, intraperitoneal, intracerebral, intraventricular, intracerebroventricular, intrathecal, intracisternal, intraspinal and/or peri-spinal routes of administration by delivery via intracranial or intravertebral needles and/or catheters with or without pump devices. The route of administration may be selected based on the therapeutic indication of the pharmaceutically active protein.

As used for administration of EPO, the phrase "therapeutically effective" or "pharmaceutically active" is generally from about 1 to 10000 I.U./kg, preferably from about 50 to 2000 I.U./kg, more preferably from about 50 to 600 I.U./kg, and most preferably from about 50 to 300 I.U./kg body weight especially when erythropoietin is administered subcutaneously. Advantageously, the formulations of the present invention may be administered to a responding subject at any desired frequency or time interval between administrations without reduced efficacy. In a preferred dosing regimen, the subject is administered the sustained release formulations of the present invention thrice per two weeks, once per week, once per two weeks, once per three weeks, once per month, once per five weeks, once per six weeks, or at more frequent or less frequent intervals, or at any combination of frequencies or time intervals as desired. The effective daily dosing of erythropoietin (EPO) is preferably from about 4000 to about 9000 I.U. (equivalent to about 60,000 I.U. to about 120,000 I.U. every two weeks). Most preferably the effective daily dosing of erythropoietin (EPO) is 5715 I.U. (equivalent to about 80,000 I.U. every two weeks). A preferred dosing regimen may be once per three weeks, particularly for subjects receiving chemotherapy for the treatment of cancer, since many chemotherapeutic regimens are administered on a once per three-week schedule. However, any dosing schedule of a therapeutic protein, such as EPO, formulated according to the present invention, can be easily coordinated with regular visits to the treating physician or with the dosing schedule of another agent, such as an anti-tumor agent, as is desirable for the patient. This allows the EPO regimen and the chemotherapeutic regimen to be administered simultaneously or in parallel, providing an economic and desirable benefit for the subject. EPO administration is delayed or withheld if the patient, male or female, exhibits a hemoglobin level in excess of about 18 g/dL for a human male and about 16 g/dL for a human female.

For therapeutic purposes, the term "jointly active amount" as used herein, means that amount of each active compound or pharmaceutical agent, alone or in combination, that elicits the desired biological or medicinal response in a tissue system, animal or human that is being sought by a researcher, veterinarian, medical doctor or other clinician, which includes alleviation of the symptoms of the disease or disorder being treated. Particularly, the biological or medicinal response is inhibition of dephosphorylation of the EPOR, or prolongation or enhancing of phosphorylation of the EPOR.

The compounds of the present invention may also be present in the form of a pharmaceutically acceptable salt or salts. For use in medicine, the salt or salts of the compounds of this invention refer to non-toxic "pharmaceutically acceptable salt or salts." Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative basic/cationic salts include, but are not limited to, benzathine, chloroprocaine, choline, diethanolamine, ethylenediamine, meglumine, procaine, aluminum, calcium, lithium, magnesium, potassium, sodium, or zinc.

Method of Identifying a Compound Useful for Treating a Nervous System Condition Related to EPOR The invention further provides efficient methods of identifying compounds that are useful for treating a nervous system condition related to EPOR Generally, the methods involve identifying compounds that decrease: 1) the expression of a SHP1 protein; or 2) the tyrosine phosphatase activity of a SHP1 protein.

The compound identification methods can be in conventional laboratory format or adapted for high throughput. The term "high throughput" refers to an assay design that allows easy screening of multiple samples simultaneously, and capacity for robotic manipulation. Another desired feature of high throughput assays is an assay design that is optimized to reduce reagent usage, or minimize the number of manipulations in order to achieve the analysis desired. Examples of assay formats include 96-well or 384-well plates, levitating droplets, and "lab on a chip" microchannel chips used for liquid handling experiments. It is well known by those in the art that as miniaturization of plastic molds and liquid handling devices are advanced, or as improved assay devices are designed, that greater numbers of samples may be performed using the design of the present invention.

Candidate compounds encompass numerous chemical classes, although typically they are organic compounds. Preferably, they are small organic compounds, i.e., those having a molecular weight of more than 50 yet less than about 2500. Candidate compounds comprise functional chemical groups necessary for structural interactions with polypeptides, and typically include at least an amine, carbonyl, hydroxyl or carboxyl group, preferably at least two of the functional chemical groups and more preferably at least three of the functional chemical groups. The candidate compounds can comprise cyclic carbon or heterocyclic structure and/or aromatic or polyaromatic structures substituted with one or more of the above-identified functional groups. Candidate compounds also can be biomolecules such as peptides, saccharides, fatty acids, sterols, isoprenoids, purines, pyrimidines, derivatives or structural analogs of the above, or combinations thereof and the like. Where the compound is a nucleic acid, the compound typically is a DNA or RNA molecule, although modified nucleic acids having non-natural bonds or subunits are also contemplated.

Candidate compounds are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Candidate compounds can also be obtained using any of the numerous approaches in combinatorial library methods known in the art, including: biological libraries; spatially addressable parallel solid phase or solution phase libraries: synthetic library methods requiring deconvolution; the "one-bead one-compound" library method; and synthetic library methods using affinity chromatography selection (Lam (1997) *Anticancer Drug Des.* 12:145). Alternatively, libraries of natural compounds in the form of bacterial, fungal, plant and animal extracts are available or readily produced. Additionally, natural and synthetically produced libraries and compounds can be readily modified through conventional chemical, physical, and biochemical means.

Further, known pharmacological agents may be subjected to directed or random chemical modifications such as acylation, alkylation, esterification, amidification, etc. to produce structural analogs of the agents. Candidate compounds can be selected randomly or can be based on existing compounds that bind to and/or modulate the tyrosine phosphatase activity of SHP1. Therefore, a source of candidate agents is libraries of molecules based on the known SHP1 inhibitors, in which the structure of the compound is changed at one or more positions of the molecule to contain more or fewer chemical moieties or different chemical moieties. The structural changes made to the molecules in creating the libraries of analog activators/inhibitors can be directed, random, or a combination of both directed and random substitutions and/or additions. One of ordinary skill in the art in the preparation of combinatorial libraries can readily prepare such libraries based on the existing SHP1 inhibitors.

A variety of other reagents also can be included in the mixture. These include reagents such as salts, buffers, neutral proteins (e.g., albumin), detergents, etc. that may be used to facilitate optimal protein-protein and/or protein-nucleic acid binding. Such a reagent may also reduce non-specific or background interactions of the reaction components. Other reagents that improve the efficiency of the assay such as protease inhibitors, nuclease inhibitors, antimicrobial agents, and the like may also be used.

1. Identify Compounds that Decrease SHP1 Expression.

As used herein, "compounds that decreases the SHP1 protein expression" include compounds that decrease SHP1 gene transcription and/or translation. The invention provides a method of identifying such a compound, which comprises the steps of contacting a compound with a regulatory sequence of the SHP1 gene or a cellular component that subsequently binds to the regulatory sequence; and determining the effect of the compound on the expression of a gene controlled by the regulatory sequence; wherein the regulatory sequence of the SHP1 gene is either within a host cell or in a cell-free system. The term "regulatory sequence" is as defined supra.

In a preferred embodiment, the method involves a regulatory sequence of the SHP1 gene within a host cell, preferably a cell of the nervous system. The cell-based assay comprises the step of: (1) contacting a compound with a cell having a regulatory sequence for a SHP1 gene or a cellular component that binds to the regulatory sequence for a SHP1 gene; (2) measuring the effect of the compound on the expression of a SHP1 or a reporter gene controlled by the regulatory sequence; and (3) comparing the effect of the compound with that of a reference control.

The host cell can be a native SHP1 host cell, or a recombinant host cell. The reference control contains only the vehicle in which the testing compound is dissolved. Several assay methods can be used to measure the effect of the compound on the expression of the SHP1 or reporter gene inside a cell. For example, gene or protein fusions comprising the regulatory sequence for a SHP1 linked to a reporter gene can be used. As used herein, "a reporter gene" refers to a gene encoding a gene product which can be measured using conventional lab techniques. Such reporter genes include but are not limited to genes encoding green fluorescent protein (GFP), β-galactosidase, luciferase, chloramphenicol acetyltransferase, β-glucuronidase, neomycin phosphotransferase, and guanine xanthine phosphoribosyl-transferase. The gene fusion is constructed such that only the transcription of the reporter gene is under control of the SHP1 regulatory sequence. The protein fusion is constructed so that both the transcription and translation of the reporter gene protein are under control of the SHP1 regulatory sequence. Preferably, a second gene or protein fusion comprising the same reporter gene but a different regulatory sequence (i.e., a regulatory sequence for a gene unrelated to SHP1 family) can be used to increase the specificity of the assay.

The effect of the compound on the expression of the reporter gene, such as GFP, can be measured by methods known to those skilled in the art. For example, the effect of the compound on expression of GFP can be measured as the effect of the compound on emissions of green fluorescence from the cell using a fluorometer. Alternatively, a cellular phenotype attributed to a SHP1, such as the phosphorylation level of Jak2 or EPOR, can also be used to measure the effect of the compound on the expression of the SHP1 protein. In addition, the effect of the compound can be assayed by measuring the amount of SHP or reporter mRNA or protein inside the cell directly using methods such as Northern Blot, RT-PCR, SDS-PAGE, Western Blot, etc., which are known to those skilled in the art.

Note that the cell-based method described supra not only identifies compounds that regulate SHP1 expression directly via binding to the regulatory sequence of a SHP1 gene, but also identifies compounds that regulate SHP1 expression indirectly via binding to other cellular components whose activities influence the SHP1 expression. For example, compounds that modulate the activity of a transcriptional activator or inhibitor for SHP1 genes can be identified using the method described herein.

In another embodiment, the method involves a regulatory sequence of the SHP1 gene in a cell-free assay system. The cell-free assay comprises the step of: (1) contacting a compound to the regulatory sequence for a SHP1 gene or a cellular component that binds to the regulatory sequence for a SHP1 gene in a cell-free assay system; (2) measuring the effect of the compound on the expression of the SHP1 or reporter gene controlled by the regulatory sequence; and (3) comparing the effect of the compound with that of a reference control. The reference control contains only the vehicle in which the testing compound is dissolved. Examples of the cell-free assay system include the in vitro translation and/or transcription system, which are known to those skilled in the art. For example, the full length SHP1 cDNA, including the regulatory sequence, can be cloned into a plasmid. Then, using this construct as the template, SHP1 protein can be produced in an in vitro transcription and translation system. Alternatively, synthetic SHP1 mRNA or mRNA isolated from SHP1 protein producing cells can be efficiently translated in various cell-free systems, including but not limited to wheat germ extracts and reticulocyte extracts. The effect of the compound on the expression of the SHP1 or reporter gene controlled by the regulatory sequence can be monitored by direct measurement of the quantity of SHP1 or reporter mRNA or protein using methods described supra.

2. Identify an Inhibitor for a SHP1 Tyrosine Phosphatase Activity

An "inhibitor" for a SHP1 tyrosine phosphatase activity refers to an inhibitory molecule identified using in vitro and in vivo assays for SHP1 tyrosine phosphatase activity. In particular, "inhibitors", refer to compounds that decrease, block, prevent, delay activation, inactivate, desensitize or down regulate SHP1 tyrosine phosphatase activity, or speed or enhance deactivation of the SHP1 tyrosine phosphatase activity.

The invention further provides a method of identifying an inhibitor of a SHP1 tyrosine phosphatase activity, comprising the steps of:

1) contacting a test compound with a SHP1 protein or an active fragment thereof; and
2) determining the ability of the test compound to decrease the tyrosine phosphatase activity of SHP1.

The amount of time necessary for contacting the test compound with the SHP1 protein is empirically determined, for example, by running a time course with a known SHP1 inhibitor, and measuring the tyrosine phosphatase activity of SHP1 as a function of time.

A variety of assay methods can be used to determine the effect of the compound on the tyrosine phosphatase activity of SHP1. Some of the assay methods are disclosed in WO99/54450. For example, SHP1 phosphotase activity can be measured as a function of the ability of SHP1 to dephosphorylate a substrate, such as a phosphorylated JAK2. In particular, a phosphorylated peptide derived from JAK2. The dephosphorylation reaction can be monitored using a malachite green assay (Lanzetta et al., *Anal Biochem.* 1979, 100:95–7), which measures the release of inorganic phosphate from the substrate. Alternatively, SHP1 phosphotase activity can be measured in vivo by changes in cellular physiology affected by the SHP1 phosphotase activity, such as the inactivation of the EPOR signal transduction pathway.

Alternatively, binding assays can be used to identify to a compound that binds to a SHP1 protein, and potentially is capable of inhibiting the phosphatase activity of SHP1. One exemplary method of such a binding assay comprises the steps of:

1) combining a test compound, a labeled ligand for a SHP1 protein, and a SHP1 protein or an active fragment thereof, and
2) measuring the binding of the test compound to the SHP1 protein or active fragment thereof by a reduction in the amount of labeled ligand binding to the SHP1 protein or active fragment thereof.

The amount of labeled ligand binding to the SHP1 protein or active fragment thereof can be measured by separating the SHP1 from unbound labeled ligand. The separation can be accomplished in a variety of ways. Conveniently, at least one of the components is immobilized on a solid substrate, from which the unbound components may be easily separated. The solid substrate can be made of a wide variety of materials and in a wide variety of shapes, e.g., microtiter plate, microbead, dipstick, resin particle, etc. The substrate preferably is chosen to maximize signal to noise ratios, primarily to minimize background binding, as well as for ease of separation and cost.

Separation may be effected for example, by removing a bead or dipstick from a reservoir, emptying or diluting a reservoir such as a microtiter plate well, or rinsing a bead, particle, chromatographic column or filter with a wash solution or solvent. The separation step preferably includes multiple rinses or washes. For example, when the solid substrate is a microtiter plate, the wells may be washed several times with a washing solution, that typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

The ligand for SHP1 can be a polypeptide that binds specifically to SHP1, such as an antibody for SHP1, or chemical compound that binds specifically to SHP1. A wide variety of labels can be used to label the SHP1 ligand, such as those that provide direct detection (e.g., radioactivity, luminescence, optical or electron density, etc), or indirect detection (e.g., epitope tag such as the FLAG epitope, enzyme tag such as horseradish peroxidase, etc.).

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, streptavidin-biotin conjugates, etc. Methods for detecting the labels are well known in the art.

The SHP1 protein or active fragment thereof can be substantially purified, or expressed from a host cell. The term "cell" refers to at least one cell, but includes a plurality of cells appropriate for the sensitivity of the detection method. Cells suitable for the present invention may be a cell of the nervous system that expresses SHP1 endogenously, or a recombinant cell, such as a bacterial, yeast, or eukaryotic cell, that expresses SHP1 recombinantly.

In preferred embodiments of the invention, the methods of identifying a compound useful for treating a nervous system condition related to EPOR, further comprise the steps of
 a) contacting a neuronal cell with the test compound;
 b) inducing neurotoxicity in the neuronal cell;
 c) assaying the cell survival rate in the presence of the test compound, and comparing the cell survival rate with that of a control wherein the neuronal cell is not treated with the test compound.

Neurotoxicity in the neuronal cells can be induced by a variety of methods known to those skilled in the art. For example, neurotoxicity in a primary hippocampal neuron. can be induced by challenging the hippocamapal neurons with glutamate. Such methods are known in the art.

The survival rate of the neuronal cells can be measured by a variety of methods known to those skilled in the art. For example, the survival rate of the neuronal cells can be measured using trypan blue exclusion assay.

Compounds of Formula I, II, and III were identified as inhibitors for SHP1 tyrosine phosphatase activity using methods of the invention.

Compound of Formula I

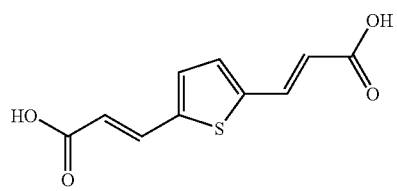

inhibited SHP1 phosphatase activity with an $IC_{50}$ of 22 µM under the assay conditions. Studies related this compound have been described previously (Safarik et al., *Spectroscopy Letters* (1999), 32(3), 443–462; Malesevic et al., *Heterocycles* (1995), 41(12), 2691–9; Karminski-Zamola et al., *Heterocycles* (1994), 38(4), 759–67).

Compound of Formula II

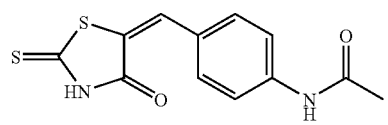

inhibited SHP1 phosphatase activity with an $IC_{50}$ of 25.7 µM under the assay conditions. Studies related to this compound have been described previously (for example in JP 92-129774).

Compound of Formula III

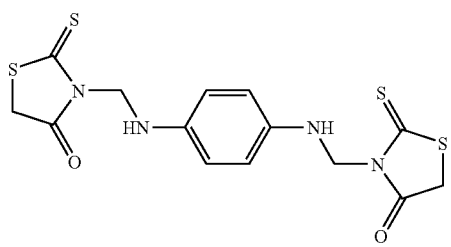

inhibited SHP1 phosphatase activity with an $IC_{50}$ of 4.3 µM under the assay conditions.

The following examples illustrate the present invention without, however, limiting the same thereto.

EXAMPLE 1

Isolation and Culturing of Primary Cells

A Rat was sacrificed at eighteen days post-coitus (d.p.c.). Rat embryos were isolated and the brains dissected in ice cold Hanks Balanced Salt Solution (HBSS). The meninges were carefully dissected away and the outer layer of frontal cortex removed and placed in 0.05 trypsin EDTA for twenty minutes. The trypsin was then removed and the tissue triturated in plating media (DMEM w/10% FBS, 1% Penicillin/streptomycin). The dissociated cells were then plated on the appropriate substrate coated culture dishes in plating media.

Primary cortical neurons were cultured on poly-d-lysine coated culture ware (BIOCOAT from Beckton Dickson) for twenty-four hours in plating media then transferred to Neurobasal media (LTI) containing 1×B-27 serum free supplement (LTI) and 1% Penicillin/streptomycin. After three days in the culture, cells were treated with 1 μM Cytosine β-D-Arabino-Furanoside (ARAC) to further select for neurons over non-neuronal cells. The neurons were cultured in the ARAC containing media for three additional days (seven days total in culture) before being used for experiments. On the day of the experiment, cultures were changed to B-27 free media for six hours. EPO (10 pM) was then added to the cultures for the appropriate time interval.

UT-7 cells were obtained from the New York Blood Center and cultured according to [12]. Briefly UT-7 cells were grown in Iscove's media (Life Technologies) containing 10% fetal bovine serum (FBS), 1% Penicillin/streptomycin, and 1 U/ml rhEPO. EPO was removed from the cultures twenty-four hours prior to the experiment. On the day of the experiment, the cells were changed to Iscove's serum free media for four hours, and then stimulated with EPO (2.5 nm or 0.25 nm) for the appropriate time interval.

Primary Astrocytes were isolated as described above and plated on un-coated tissue culture plastic dishes in plating media. Cultures of primary rat astrocytes were obtained by leaving the cells in plating media for fourteen days, changing the media every four days. At the end of fourteen days, the cells were used for analysis.

EXAMPLE 2

Lysate Preparation and Western Analysis

The precise control of signaling through receptor pathways requires the proper control of activation and inactivation events to initiate and terminate signaling. Activation events such as changes in receptor conformation or phosphorylation state are balanced by termination events such as receptor internalization, a return to basal conformation, enzymatic processes that return the receptor to its basal phosphorylation state or some combination of these events. Some ligand-receptor systems make use of feedback mechanisms to regulate their own activity [19] thereby providing an additional level of control over their signaling activity.

According to the present invention, 1) EPO causes the phosphorylation of the EPO receptor and this phosphorylation is sustained relative to hematopoietic cells, 2) the phosphorylation of the downstream targets of EPO signaling ERK1/ERK2 is also sustained and 3) the expression of the negative regulator SHP1 is decreased following treatment with EPO. The observed changes in expression, and thereby the activity of SHP1 as a result of EPO can be responsible, at least in part, for one of the unique properties of EPO, namely its increased potency, in neurons.

Cells were lysed with lysis buffer (20 mM Hepes, 7.9, 10 mM KCl, 0.1 mM NaVO$_4$, 1 mM EDTA, 1 mM EGTA, 0.2% NP-40, 10% Glycerol, 0.2 mM PMSF) for ten minutes on ice Extracts were spun at 15,000 rpm for two minutes and the supernatants were subjected to SDS-PAGE. Samples were transferred to nitrocellulose membrane (IMMOBILON-P, Millipore) and blocked with TBS-T (20 mM Tris-Ci, pH 7.6, 150 mM NaCl, 0.1% Tween-20) containing 1% FBS. Membranes were subsequently probed with antibodies against SHP-1 (mouse monoclonal from Transduction Laboraties) or Erk1/2 (p44/42) (rabbit polyclonal from Cell Signaling). A secondary antibody, conjugated to horseradish peroxidase was used to detect the proteins and the immunoreactive bands were visualized using a chemiluminescence kit (Amersham Pharmacia Biotech, Piscataway, N.J.).

Cell lysis and immunoprecipitation was carried out as previously described [16]. Briefly, cells were lysed with lysis buffer (10 mM Tris-Cl, pH 8.0, 150 mM NaCl, 5 mM EDTA, 10% Glycerol, 1 mM sodium vanadate, 1% Igepal CA-630, protease/phosphatase inhibitor cocktails from Sigma). After fifteen minutes on ice, the extracts were centrifuged for ten minutes at 15,000 rpm and the supernatants were used for immunoprecipitation. Anti-EPO receptor antibody (Maine Biotech) was incubated with the cell extracts for one and one-half hours at 4° C. and then rocked for one hour with G-sepharose beads. After one hour, the mixture was washed twice with lysis buffer and once with lysis buffer containing 0.1% Igepal CA-630 (NP40). The samples were subsequently boiled in Laemlli sample buffer and subjected to SDS-PAGE and immunoblotting.

EPO treatment results in sustained activation of the MAP Kinase pathway as seen by phosphorylation of ERK1/ERK2. Primary cortical neurons were cultured for seven days in Neurobasal media containing B-27 serum free supplement. The cells were changed to B-27 free media for six hours prior to the experiment to decrease basal phosphorylation of ERK1/ERK2. EPO was added to the neurons at a concentration of 10 pm. Preparation of lysates and subsequent analysis with SDS-PAGE showed that the phosphorylation of ERK1/ERK2 was detectable at very low levels by 1 hr and increased up to six hours (FIG. 1). The phosphorylation reached a maximum at six hours then decreased to near basal levels by twenty-four hours. In contrast, the phosphorylation of ERK1/ERK2 in UT-7 cells in response to EPO (2.5 nm, 0.25 nm) was detectable by five minutes and reached a maximum at fifteen minutes. By thirty minutes, the phosphorylation of ERK1/2 had diminished to near undetectable levels (FIG. 1).

Previous reports have implicated the ERK1/ERK2 pathway in neuroprotection. Glutamate has been reported to increase the phosphorylation of ERK1/ERK2 [29] and inhibitors of the ERK1/ERK2 kinase pathway have been shown to be neuroprotective [23, 2, 25]. Thus the sustained activation of the ERK1/ERK2 pathway by EPO seems to contradict its role as a neuroprotectant. However, the activation of ERK1/ERK2 may not be as important for EPO mediated neuroprotection as the eventual inactivation of this pathway. According to the present invention, the phosphorylation of ERK1/ERK2 was terminated by twenty-four fours following EPO treatment; the phosphorylation of ERK1/ERK2 began to decrease even though the EPO receptor was still phosphorylated. The decrease in ERK1/ERK2 is most likely due to a mechanism different than the inactivation of the EPOR signal and involves a separate process such as depletion of ERK1/ERK2 or a process that might or might not be mediated by EPO directly.

Figure 2:
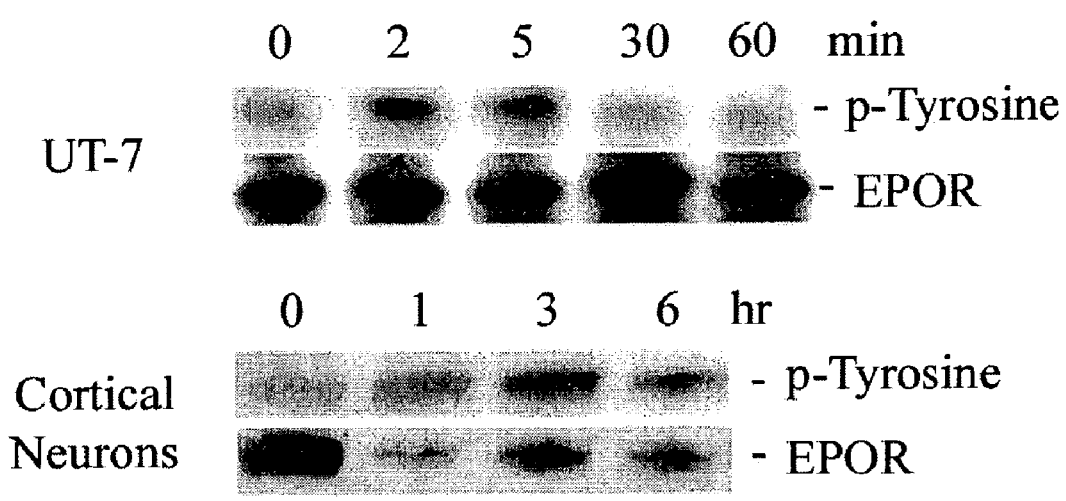
FIG. 2: Illustrates a sustained phosphorylation of EPOR in neurons treated with EPO as compared to that in hematopoietic cells treated with EPO. Primary cortical neurons and hematopoietic cells UT-7 were treated with EPO for the indicated time then harvested. Cell extracts were immunoprecipitated with anti-EPOR antibody and blotted with either an anti-EPOR antibody or an anti-phosphotyrosine antibody. The time course of EPOR phosphorylation in neurons or UT-7 cells treated with EPO was plotted.

EPO treatment results in the sustained activation/phosphorylation of the EPO receptor in primary neurons. Primary cortical neurons and UT-7 cells were treated with EPO and immunoprecipitated with the EPOR antibody. The preparations were then subjected to SDS-PAGE and the phosphorylated EPOR was detected using an anti-p-tyrosine antibody. Treatment of cortical neurons with EPO (10 pm) resulted in an increased phosphorylation of the EPOR that was detectable by one hour and persisted to six hours after treatment (FIG. 2). In contrast, treatment of UT-7 cells with EPO (2.5 nm) resulted in a rapid, transient phosphorylation of the EPOR that was detectable by two minutes, peaked at ten minutes, and returned to near basal levels by thirty minutes (FIG. 2).

Figure 5:
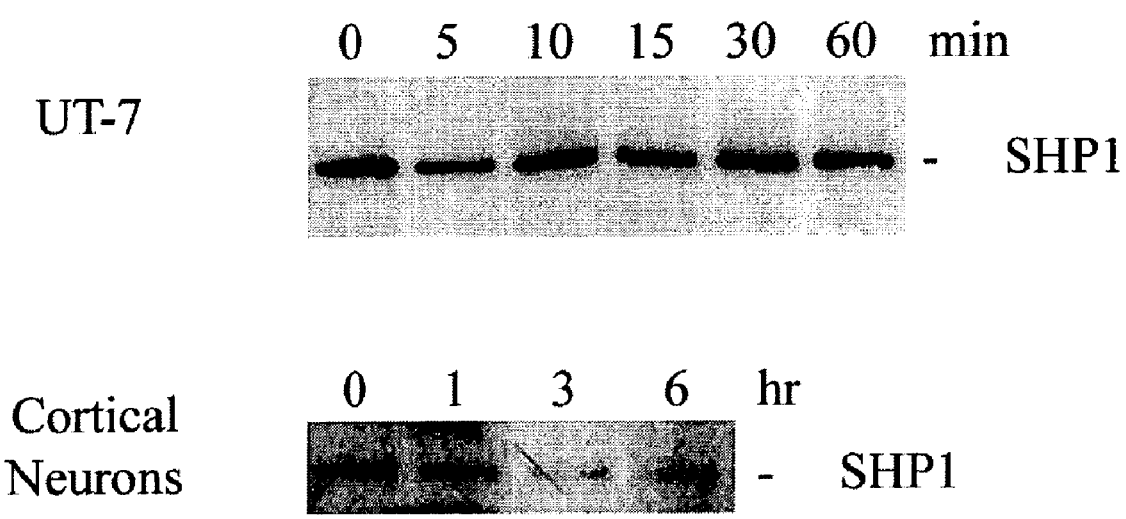
FIG. 5: Demonstrates that following treatment with EPO, SHP1 protein levels decreased with time in neurons, but maintained the same in UT-7 cells. Primary cortical neurons and hematopoietic cells UT-7 were stimulated with EPO (2.5 nM and 10 pM respectively) for the indicated time points. Cell extracts were collected and subject to SDS-PAGE and immobilized in a nylon membrane. Blots were then probed with and an antibody against SHP1. A decrease in the level of SHP1 protein was detectable at 3 hours and 6 hours in cortical neurons. No detectable change in SHP1 levels was observed in UT-7 cells treated with EPO.

EPO decreases the expression of SHP1 protein in primary cortical neurons. Since there is a decrease in SHP1 mRNA expression in cortical neurons, we sought to determine if that translated into a decrease in protein levels. Primary cortical neurons and UT-7 cells were treated with 10 pm EPO and 2.5 nM EPO respectively. Cells were lysed, subjected to SDS-PAGE, and Western blots were probed with an antibody to SHP1. As with mRNA expression, SHP1 protein in primary cortical neurons is seen to decrease over the 6 hour interval (FIG. 5). In UT-7 cells, addition of EPO did not change SHP1 protein levels which remained constant through 1 hour (FIG. 5).

EXAMPLE 3

RNA Isolation and RT-PCR

Primary cortical neurons and UT-7 cells were cultured as described above. Following EPO treatment total RNA was isolated using the RNAeasy kit (Qiagen). RNA was then quantitated and 2.5 µg was used to make first strand cDNA using the Superscript™ Preamplification System (Gibco-BRL). PCR was then carried out on the first strand cDNA using oligonucleotide primers designed against human rat shp-1. To control for cDNA content, GAPDH was amplified simultaneously. The target molecules were amplified following oligonucleotide primers: human SHP-1 (5'-ttcctg-gaccagatcaaccag (SEQ ID NO:6) and 3'-cttcctcttgagggac-cacttgc SEQ ID NO:1), Rat SHP-1 (5'-aaaggccggaacaaatgtgt (SEQ ID NO:2) and 3'-ggatgg tcttctggatgtca (SEQ ID NO:3)), and Rat GAPDH (5'-ggagtctactggcgtcttcac (SEQ ID NO:4) and 3'-aaggccatgccagtgagcttc (SEQ ID NO:5)).

Figure 3:
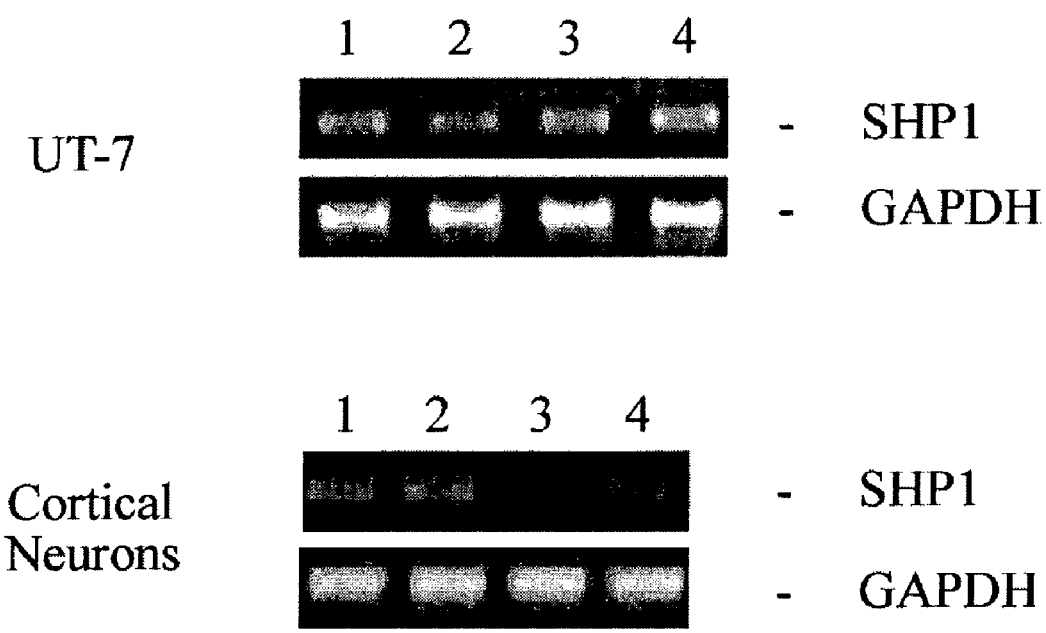
FIG. 3: Demonstrates that following treatment with EPO, SHP1 mRNA levels decreased dose dependantly in neurons, but maintained the same in hematopoietic cells. Primary cortical neurons and hematopoietic cells UT-7 were left (1) untreated or treated with (2) 100 fM, (3) 10 pM or (4) 1 nM EPO for 24 hours. Total RNA was isolated and levels of mRNA for SHP1 and the housekeeping gene Glyceraldehye-3-phosphate dehydrogenase (GAPDH) were determined using RT-PCR. SHP1 mRNA levels showed a dose dependant decrease following treatment with EPO in neurons. SHP1 mRNA levels were unchanged in EPO treated UT-7 cells.
Figure 6:
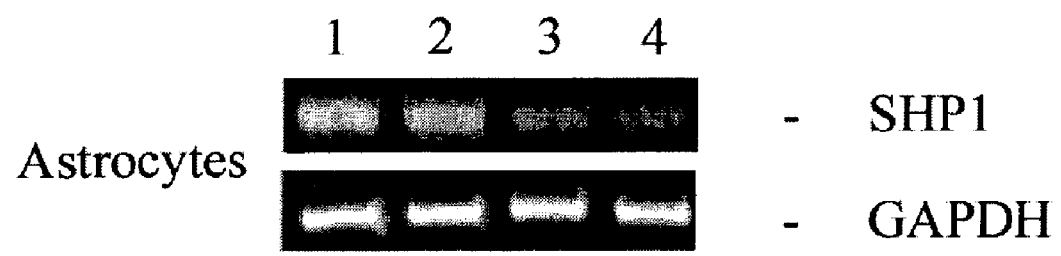
FIG. 6: Illustrates that EPO caused a dose dependant decrease in SHP1 mRNA in non-neuronal nervous cell astrocytes with the most significant changes at 10 pM and 1 nM. Primary astrocytes were (1) left untreated or treated with (2) 100 fM, (3) 10 pM or (4) 1 nM EPO for 24 hours. Total RNA was isolated and subjected to RT-PCR to determine levels of SHP1 mRNA. EPO caused a dose dependant decrease in SHP1 mRNA in astrocytes with the most significant changes at 10 pM and 1 nM.
Figure 7:
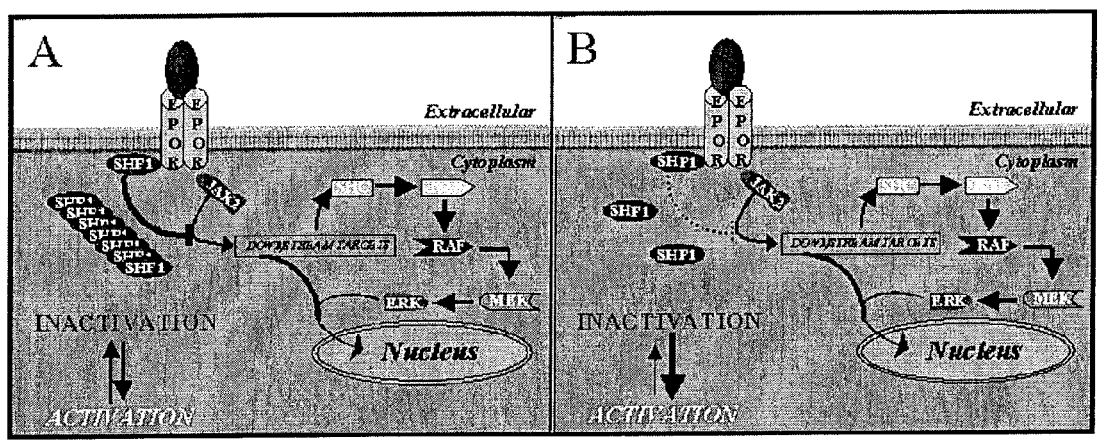
FIG. 7, Panels A and B.

EPO induces a dose dependant decrease in the expression of SHP1 mRNA in primary neurons and in primary astrocytes. To determine a possible mechanism for the sustained phosphorylation of EPO targets in neurons the expression of SHP1, a negative regulator of EPO receptor phosphorylation was examined. Primary Neurons and astrocytes cultured as described above were treated with EPO (100 fm, 10 pm, 1 nm). Total RNA was isolated and then subjected to RT-PCR, using primers for the Rat SHP1 to determine SHP1 mRNA expression levels. RAT GAPDH served as a control. Twenty-four hours of pre-treatment of EPO at 10 pm or 1 nm resulted in a decrease in the expression of SHP1 mRNA in primary cortical neurons (FIG. 3). EPO at 100 fm did not alter the expression level of SHP1. Similarly, in astrocytes, a dramatic decrease in SHP1 mRNA is seen in 10 pM and 1 nM EPO treated cells. 100 fM EPO does not affect expression levels (FIG. 6). In UT-7 cells, three hours of pre-treatment of EPO (2.5 nm) resulted in an increase of SHP1 mRNA. However, in comparison with the three hour pre-treatment, cells pre-treated with EPO for six or twenty-four hours did not show any difference.

The potential implications of EPO's attenuation of SHP1 expression in the CNS can be significant. EPO's increased potency in neurons, combined with the sustained activation of its signal can be important considering the relatively low concentrations of EPO that are present in the CNS [8] and the low amounts that can cross the blood brain barrier and enter the CNS from the systemic circulation. Enhancing the signal can be a way by which the brain can best make use of the EPO that is available to it.

SHP1 has also been suggested to function as a positive signaling molecule in non-neuronal cells of the nervous system. Astrocytes and microglia have been reported to rely on SHP1 for activation. Previous reports have demonstrated that astrocytes and microglia express EPOR suggesting that these cell types can be responsive to EPO [24]. According to the present invention, EPO decreases the expression of SHP1 in astrocytes in a dose dependant manner. The activation of astrocytes and microglia has been implicated in damage to the CNS associated with a number of pathological conditions including bacterial infection [9], Alzheimers disease [17], and focal brain injury [32, 15, 31]. The mechanism by which astrocytes and microglia contribute to neural damage remains unclear but may be due in part to their release of cytokines following activation and their contribution to the inflammatory response in the injured brain. The ability of EPO to decrease SHP1 expression can attenuate the positive signal that leads to the activation of these non-neuronal cells, thereby preventing the damage that is associated with them. The observation that EPO has a similar effect on the expression of SHP1 in astrocytes provides evidence that EPOs actions in the CNS are not limited to neuronal cells.

Figure 4:
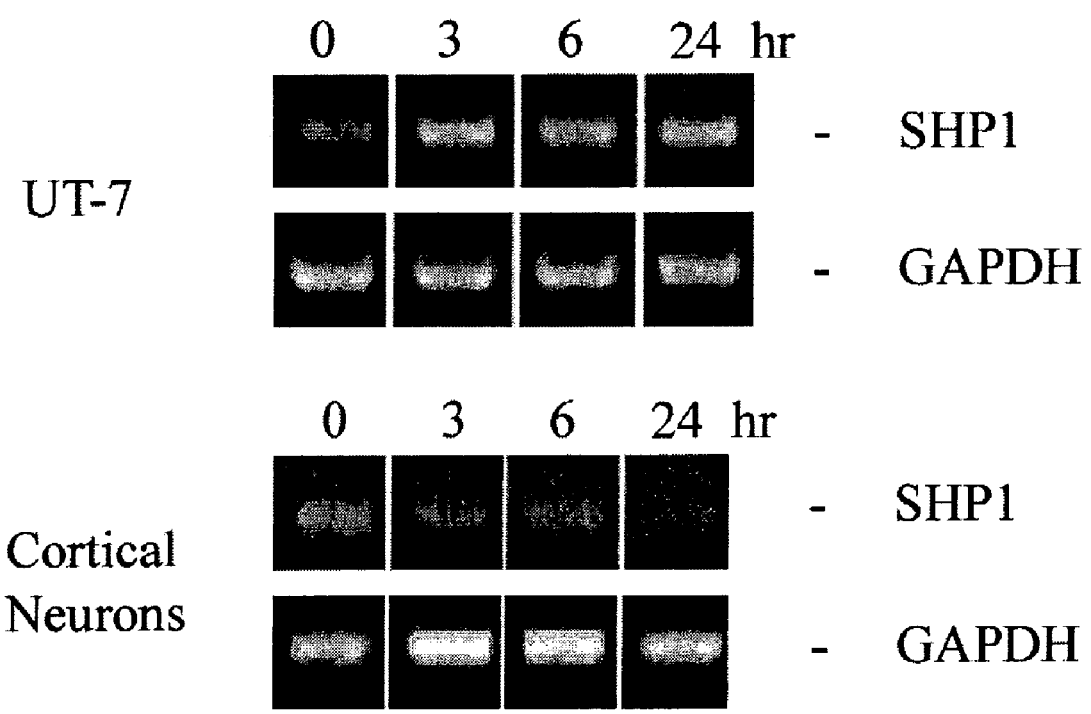
FIG. 4: Shows that following treatment with EPO for time periods lasting from 3 hours to 24 hours, SHP1mRNA levels continued to decrease in neurons while remained the same in hematopoietic cells. Primary cortical neurons and hematopoietic cells UT-7 were stimulated with EPO (2.5 nM and 10 pM respectively) for 3, 6, or 24 hours. Total RNA was subjected to RT-PCR to determine mRNA levels of SHP1 and GAPDH. EPO treatment caused a decrease in SHP1mRNA levels by 3 hours and continued to decrease out to 24 hours. SHP1 mRNA levels in UT-7 cells remained unchanged following treatment with EPO.

A decrease in SHP1 mRNA expression is detectable in cortical neurons following three hour exposure to EPO. The expression of SHP1 mRNA was examined in primary cortical neurons and UT-7 cells treated with EPO (10 pm) for three, six or twenty-four hours to determine the time to induce a change in SHP1 mRNA expression. In primary neurons, a decrease in SHP1 mRNA expression was detectable after three hours of exposure to EPO. SHP1 expression continued to decrease at six hours and was virtually undetectable by twenty-four hours (FIG. 4). EPO did not cause a decrease in SHP1 expression in UT-7 cells. In fact, the amounts of SHP1 mRNA seemed to increase by three hours and remain elevated out to twenty-four hours (FIG. 4).

REFERENCES

1. Alafaci et al., "Effect of Recombinant Human Erythropoietin on Cerebral Ischemia Following Experimental Subarachnoid Hemorrhage", *Eur. J. Pharmacol.* (2000) 406:219–225.
2. Alessandrini et al., "MEK1 Protein Kinase Inhibition Protects Against Damage Resulting from Focal Cerebral Ischemia", *P.N.A.S. USA* (1999) 96:12866–12869

3. Bernaudin et al., "A Potential Role for Erythropoietin in Focal Permanent Cerebral Ischemia in Mice", *J. Cereb. Blood Flow Metab.* (1999) 19:643–651
4. Bittorf et al., "Induction of Erythroid Proliferation and Differentiation by a Trophoblast-Specific Cytokine Involves Activation of the JAK/STAT Pathway", *J. Mol. Endocrinol.* (2000) 25:253–262
5. Brines et al., "Erythropoietin Crosses The Blood-Brain Barrier To Protect Against Experimental Brain Injury", *P.N.A.S. USA* (2000) 97:10526–10531.
6. Damen et al., "Erythropoietin Stimulates The Tyrosine Phosphorylation Of Shc And Its Association With Grb2 And A 145-Kd Tyrosine Phosphorylated Protein", *Blood* (1993) 82:2296–2303.
7. M. Digicaylioglu and S. A. Lipton, "Erythropoietin-Mediated Neuroprotection Involves Cross-Talk Between Jak2 And NF-Kb Signalling Cascades", *Nature* (2001) 412:641–647.
8. Digicaylioglu et al., "Localization of Specific Erythropoietin Binding Sites in Defined Areas of the Mouse Brain", *P.N.A.S. USA* (1995) 92:3717–3720.
9. Hanisch et al., "The Protein Tyrosine Kinase Inhibitor AG126 Prevents the Massive Microglial Cytokine Induction by Pneumococcal Cell Walls", *Eur. J. Immunol.* (2001) 31:2104–2115.
10. Horvat et al., "A Novel Role for Protein Tyrosine Phosphatase SHP in Controlling Glial Activation in the Normal and Injured Nervous System", *J. Neurosci.* (2001) 21:865–874.
11. Juul et al., "Erythropoietin and Erythropoietin Receptor in the Developing Human Central Nervous System", *Pediatr. Res.* (1998) 43:40–49.
12. Komatsu et al., "Establishment and Characterization of an Erythropoietin-Dependent Subline, UT-7/EPO, Derived From Human Leukemia Cell Line, UT-7", Blood (1993) 82:456–464.
13. Koshimura et al., "Effects Of Erythropoietin On Neuronal Activity", *J. Neurochem.* (1999) 72:2565–2572.
14. Krautwald et al., "Involvement of the Protein Tyrosine Phosphatase SHP-1 in RAS-Mediated Activation of the Mitogen-Activated Protein Kinase Pathway", *Mol. Cell. Biol.* (1996) 16:5955–5963.
15. L. T. Lau and A. C. Yu, "Astrocytes Produce And Release Interleukin-1, Interleukin-6, Tumor Necrosis Factor Alpha and Interferon-Gamma Following Traumatic and Metabolic Injury", *J. Neurotrauma* (2001) 18:351–359.
16. Lecoq-Lafon et al., "Erythropoietin Induces the Tyrosine Phosphorylation of GAB1 and its Association with SHC, SHP2, SHIP, and Phosphatidylinositol 3-Kinase", *Blood* (1999) 93:2578–2585.
17. Lue et al., "Involvement of Microglial Receptor for Advanced Glycation Endproducts (RAGE) in Alzheimer's Disease: Identification of a Cellular Activation Mechanism Inflammatory Repertoire of Alzheimer's Disease and Nondemented Elderly Microglia In Vitro", *Exp. Neurol.* (2001) 171:29–45.
18. Masuda et al., "Functional Erythropoietin Receptor of the Cells with Neural Characteristics: Comparison with Receptor Properties of Erythroid Cells", *J. Biol. Chem.* (1993) 268:11208–11216.
19. Mauschitz et al., "Self-Regulation of the Endothelin Receptor System in Choriocarcinoma Cells", *Biochim. Biophys. Acta* (2000) 1502:224–234.
20. Mizuno et al., "SHP-1 is Involved in Neuronal Differentiation of P19 Embryonic Carcinoma Cells", *FEBS Lett.* (1997) 417:6–12.
21. Morishita et al., "Erythropoietin Receptor is Expressed in Rat Hippocampal and Cerebral Cortical Neurons, and Erythropoietin Prevents In Vitro Glutamate-Induced Neuronal Death", *Neuroscience* (1997) 76:105–116.
22. Morishita et al., "Anti-Erythropoietin Receptor Monoclonal Antibody: Epitope Mapping, Quantification of the Soluble Receptor, and Detection of the Solubilized Transmembrane Receptor and the Receptor-Expressing Cells", *Blood* (1996) 88:465–471.
23. Murray et al., "Inhibition of the P44/42 MAP Kinase Pathway Protects Hippocampal Neurons in a Cell-Culture Model of Seizure Activity", *P.N.A.S. USA* (1998) 95:11975–11980.
24. Nagai et al., "Erythropoietin and Erythropoietin Receptors in Human CNS Neurons, Astrocytes, Microglia, and Oligodendrocytes Grown in Culture", *J. Neuropathol. Exp. Neurol.* (2001) 60:386–392.
25. Namura et al., "Intravenous Administration of MEK Inhibitor U0126 Affords Brain Protection Against Forebrain Ischemia and Focal Cerebral Ischemia", *P.N.A.S. USA* (2001) 98:11569–11574.
26. Ribatti et al., "Human Erythropoietin Induces a Pro-Angiogenic Phenotype in Cultured Endothelial Cells and Stimulates Neovascularization In Vivo", *Blood* (1999) 93:2627–2636.
27. Sakanaka et al., "In Vivo Evidence that Erythropoietin Protects Neurons from Ischemic Damage", *P.N.A.S. USA* (1998) 95:4635–4640.
28. A. D. Sinor and D. A. Greenberg, "Erythropoietin Protects Cultured Cortical Neurons, But Not Astroglia, from Hypoxia and AMPA Toxicity", *Neurosci. Lett.* (2000) 290:213–215.
29. Stanciu et al., "Persistent Activation of ERK Contributes to Glutamate-Induced Oxidative Toxicity in a Neuronal Cell Line and Primary Cortical Neuron Cultures", *J. Biol. Chem.* (2000) 275:12200–12206.
30. Studer et al., "Enhanced Proliferation, Survival, and Dopaminergic Differentiation of CNS Precursors in Lowered Oxygen", *J. Neurosci.* (2000) 20:7377–7383.
31. Takeuchi et al., "Macrophage Colony-Stimulating Factor is Expressed in Neuron and Microglia after Focal Brain Injury", *J. Neurosci. Res.* (2001) 65:38–44.
32. Takeuchi et al., "Microglial NO Induces Delayed Neuronal Death Following Acute Injury in the Striatum", *Eur. J. Neurosci.* (1998) 10:1613–1620.
33. Westenfelder et al., "Human, Rat, and Mouse Kidney Cells Express Functional Erythropoietin Receptors", *Kidney Int.* (1999) 55:808–820

What is claimed is:

1. A method for increasing the potency of erythropoietin (EPO) in a subject in need thereof, comprising the step of administering to the subject an effective dose of a composition that decreases the tyrosine phosphatase activity of SHP1 in a cell of the nervous system of the subject, wherein said composition is selected from the group consisting of a compound of Formula (I);

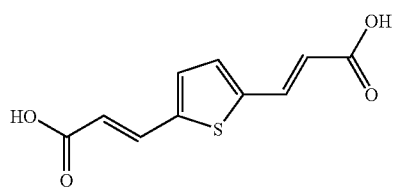

a compound of Formula (II);

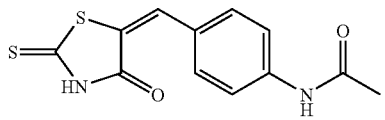

and a compound of Formula (III);

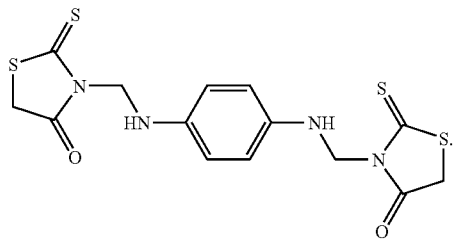

* * * * *

SEQUENCE LISTING

<160> NUMBER OF SEQ ID NOS: 6

<210> SEQ ID NO 1
<211> LENGTH: 23
<212> TYPE: DNA
<213> ORGANISM: artificial sequence
<220> FEATURE:
<223> OTHER INFORMATION: oligonucleotide primer

<400> SEQUENCE: 1
cttcctcttg agggaccact tgc                                             23

<210> SEQ ID NO 2
<211> LENGTH: 20
<212> TYPE: DNA
<213> ORGANISM: artificial  sequence
<220> FEATURE:
<223> OTHER INFORMATION: oligonucleotide primer

<400> SEQUENCE: 2
aaaggccgga acaaatgtgt                                                 20

<210> SEQ ID NO 3
<211> LENGTH: 20
<212> TYPE: DNA
<213> ORGANISM: artificial sequence
<220> FEATURE:
<223> OTHER INFORMATION: oligonucleotide primer

<400> SEQUENCE: 3
ggatggtctt ctggatgtca                                                 20

<210> SEQ ID NO 4
<211> LENGTH: 21
<212> TYPE: DNA
<213> ORGANISM: artificial sequence
<220> FEATURE:
<223> OTHER INFORMATION: oligonucleotide primer

<400> SEQUENCE: 4
ggagtctact ggcgtcttca c                                               21

<210> SEQ ID NO 5
<211> LENGTH: 21
<212> TYPE: DNA
<213> ORGANISM: artificial sequence
<220> FEATURE:
<223> OTHER INFORMATION: oligonucleotide primer

<400> SEQUENCE: 5
aaggccatgc cagtgagctt c                                               21

<210> SEQ ID NO 6
<211> LENGTH: 21
<212> TYPE: DNA
<213> ORGANISM: artificial sequence
<220> FEATURE:
<223> OTHER INFORMATION: oligonucleotide primer

<400> SEQUENCE: 6
ttcctggacc agatcaacca g                                               21